(12) United States Patent
Gross et al.

(10) Patent No.: US 6,967,219 B2
(45) Date of Patent: Nov. 22, 2005

(54) REVERSING OR PREVENTING PREMATURE VASCULAR SENESCENCE

(75) Inventors: Steven S. Gross, New York, NY (US); Michael S. Goligorsky, Stony Brook, NY (US)

(73) Assignees: Cornell Research Foundation, Inc., Ithaca, NY (US); The Research Foundation of the State University of New York, Albany, NY (US)

( * ) Notice: Subject to any disclaimer, the term of this patent is extended or adjusted under 35 U.S.C. 154(b) by 337 days.

(21) Appl. No.: 10/268,106

(22) Filed: Oct. 10, 2002

(65) Prior Publication Data

US 2003/0073747 A1 Apr. 17, 2003

Related U.S. Application Data

(60) Provisional application No. 60/328,858, filed on Oct. 12, 2001.

(51) Int. Cl.[7] .............................................. A61K 31/195
(52) U.S. Cl. ...................................... 514/565; 514/564
(58) Field of Search ................................ 514/565, 564

(56) References Cited

U.S. PATENT DOCUMENTS

| | | | |
|---|---|---|---|
| 5,140,048 A | 8/1992 | Ulrich et al. ............... | 514/601 |
| 5,478,946 A | 12/1995 | Murad et al. ............... | 435/215 |
| 6,784,178 B2 | 8/2004 | Gross et al. ................ | 514/249 |
| 2003/0086916 A1 | 5/2003 | Goligorsky et al. ....... | 424/94.4 |
| 2004/0024060 A1 * | 2/2004 | Lundstedt et al. .......... | 514/554 |

OTHER PUBLICATIONS

Dambrova et al., "N–hydroxyguanidine compound 1–(3,4–dimethoxy–2–chlorobenzylideneamino)–3–hydroxyguanidine inhibits the xanthine oxidase mediated generation of superoxide radical", Abstract , Archives of Biochem. and Biophysics, May 1, 2000, 377(1), 101–8.*

WEBSTER'S II, New Riverside University Dictionary, p. 933, 1988.*

* cited by examiner

*Primary Examiner*—Dwayne Jones

(57) ABSTRACT

Premature vascular senescence is reversed or prevented in tissue or cells by contacting the tissue or cells with a hydroxyguanidine. This finds application in treatment of patients with a disorder associated with elevated levels of advanced glycation end products in blood or tissue, e.g., patients with end stage renal disease or poorly controlled diabetes, and in contacting vascular tissue or cells ex vivo to prevent occurrence of premature senescence.

11 Claims, No Drawings

REVERSING OR PREVENTING PREMATURE VASCULAR SENESCENCE

CROSS-REFERENCE TO RELATED APPLICATION

This application claims the benefit of U.S. Provisional Application No. 60/328,858 filed on Oct. 12, 2001.

This invention was made at least in part with Government support under National Institutes of Health grants numbers DK45462 and DK54602. The Government has certain rights in the invention.

TECHNICAL FIELD

This application is directed to treating animals including humans with premature vascular senescence as manifested by elevated blood or tissue levels of advanced glycation end products, and in another embodiment, with preventing the occurrence of premature vascular senescence in vascular tissue or cells ex vivo.

BACKGROUND OF THE INVENTION

Previous to this invention, premature vascular senescence has not been associated with any specific pathological condition or considered a problem in tissue or cells ex vivo harvested for use for medical purposes.

SUMMARY OF THE INVENTION

The invention herein had its genesis in the discovery that elevated glucose levels in diabetes cause premature vascular senescence.

In one embodiment, denoted the first embodiment, the invention herein is directed at a method of treating an animal with a disorder associated with elevated levels of advanced glycation end products in blood or tissue, comprising administering to the animal a therapeutically effective amount of agent which is selected from the group consisting of premature vascular senescence ameliorating hydroxyguanidines and pharmaceutically acceptable salts thereof.

In another embodiment, denoted the second embodiment, the invention is directed at a method of preventing the occurrence of premature senescence in vascular tissue or vascular cells comprising incubating the tissue or cells with a premature vascular senescence preventing effective amount of agent selected from the group consisting of premature vascular senescence preventing hydroxyguanidines and pharmaceutically acceptable salts thereof.

As used herein, the term "premature vascular senescence" is used to mean cell cycle arrest associated with the expression of senescence associated β-galactosidase and not associated with the attrition of telomeres and is characterized by the propensity of the said cells toward apoptotic death.

As used herein, the term "animals" includes mammals including humans.

DETAILED DESCRIPTION

We turn now to the first embodiment of the invention, that is the embodiment of the invention directed at a method of treating an animal, e.g., a human patient, with a disorder associated with elevated levels of advanced glycation end products in blood or tissue, comprising administering to the animal a therapeutically effective amount of agent which is selected from the group consisting of premature vascular senescence ameliorating hydroxyguanidines and pharmaceutically acceptable salts thereof.

Elevated levels of advanced glycation end products in blood are present when elevated levels of total plasma advanced glycation end products (AGE) and/or elevated levels of pentosidine and/or elevated levels of Amadori albumin and/or elevated levels of Amadori hemoglobin (Hgb Alc), are determined.

Normal blood level of AGE is equal to or below 11.4±2.9 U/ml; elevated levels are considered to be any levels above 14.5 U/ml. Normal blood level of pentosidine is 1.63±0.07 pmol/mg protein or less with elevated levels considered to be any levels above 2 pmol/mg. Normal blood level of Amadori serum albumin is 20.9±4.0 U/ml; elevated levels are considered to be any levels above 39 U/ml. Normal level of Hgb Alc is 0.4% or less; elevated levels are considered to be any levels above 0.7%.

Total plasma AGE is determined as described in Chiavelli, F., et al, J. Pediatr. 34, 486–491.

Pentosidine level is determined using HPLC techniques as described in Sugiyama, S., et al, J. Am. Soc. Nephrol. 9, 1681–1688 (1998).

Amadori serum albumin is determined by ELISA as described in Schalkwijk, C., et al, Diabetes 48, 2446–2453 (1999).

Amadori hemoglobin (Hgb Alc) is determined using routine testing.

Elevated levels of advanced glycation end products in tissues are deemed to be present when positive immunohistochemical staining of the biopsy material can be demonstrated using antibodies against N-carboxymethyl-lysine (CML) or pentosidine, as detailed in N. Tanji et al, J. Am. Soc. Nephrol. 11: 1656–66, 2000.

Disorders associated with elevated blood or tissue levels of advanced glycation end products include chronic renal disease, poorly controlled diabetes mellitus, end stage renal disease, peripheral vascular disease, systemic lupus erythematosus and Alzheimer's disease and other neurodegenerative diseases.

End stage renal disease is characterized by creatinine clearance below 10 mg/dl, which is usually associated with severe anemia and patients are treated with, in most cases, hemodialysis or peritoneal dialysis. Poorly controlled diabetes mellitus, types 1 and 2, is characterized by abnormal glucose tolerance test, elevated fasting glucose levels (>120 mg/dl) and/or frank hyperglycemia. Active systemic lupus erythematosus is characterized by polyarthialgia, proteinuria (>200 mg/day), elevated blood pressure, and elevated titer of anti-DNA antibodies. Alzheimer's disease is characterized by the loss of cognitive functions in the absence of otherwise identifiable neurotoxic, structural or metabolic abnormalities. Chronic renal diseases are characterized by persistent proteinuria (>200 mg/day) and elevated blood pressure (>140/90 mm Hg). Peripheral vascular disease includes disorders affecting the arteries, veins and lymphatics of the extremities.

We turn now to the premature vascular senescence ameliorating hydroxyguanidines and pharmaceutically acceptable salts thereof Testing for whether a hydroxyguanidine is a premature vascular senescence ameliorating hydroxyguanidine is carried out as follows: Vascular endothelial cells are grown on a protein matrix containing advanced glycation end products, e.g., glucose-modified matrix proteins, e.g., Matrigel, in the presence or absence of the hydroxyguanidine being tested. Signs of premature cell senescence are examined following a 3–5 day interval. The hydroxyguanidine agent meets the test if premature cell senescence is ameliorated in the presence of the agent.

Alternatively, vascular endothelial cells subjected to advanced glycation end products for a period of time to induce premature cell senescence are treated with the agent being tested in the continuous presence of advanced glycation end products. The hydroxyguanidine agent meets the test if the treatment results a decrease of premature cell senescence.

The premature vascular senescence ameliorating hydroxyguanidines are preferably premature vascular senescence ameliorating agents having the formula:

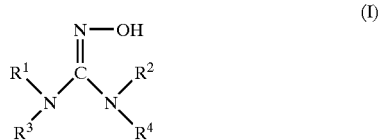

wherein $R^1$, $R^2$, $R^3$ and $R^4$ are selected to permit transport into cells and are the same or different and can be independently selected from the group consisting of hydrogen, amino, imino, alkyl, substituted alkyl, phenyl, substituted phenyl, cycloalkyl, benzyl, acyl, pyridyl, piperidyl, piperazyl, amino acid, lipid and carbohydrate and wherein $R^3$ and $R^4$ can optionally join to form a ring. The alkyl can be, for example, $C_1$–$C_{10}$ alkyl. The substituents on substituted alkyl include, for example, one or more of the same or different of halogen, thiol, nitro, amino, carboxyl, hydroxyl, cyano, $C_1$–$C_6$-alkoxy and aryl substituted on $C_1$–$C_{10}$ alkyl. The substituents on substituted phenyl include, for example, one or more of the same or different of halogen, thiol, nitro, amino, carboxyl, hydroxyl, cyano, $C_1$–$C_6$ alkyl, and $C_1$–$C_6$ alkoxy (e.g., methoxy). The cycloalkyl can contain, for example, from 3 to 8 carbon atoms. The acyl can be, for example, $C_1$–$C_6$ acyl. The halogens include chloro, bromo, fluoro and iodo.

The pharmaceutically acceptable salts include, for example, the protonated structure (I) where the counterion is, for example, hydrochloride, acetate or sulfate. Other pharmaceutically acceptable counterions will be obvious to those skilled in the art.

Preferably at least one of $R^1$, $R^2$, $R^3$ and $R^4$ is hydrogen, and very preferably two or three of $R^1$, $R^2$, $R^3$ and $R^4$ are hydrogen.

When one or both of $R^3$ and $R^4$ are alpha-amino acids, the alpha-amino acid can be an L-compound or D-compound or D,L-compound. L-compounds are preferably used but D-compounds and D,L-compounds also can be used.

The hydroxyguanidine treating agents include, for example, $N^\omega$-hydroxyarginine and hydroxyguanidine.

$N^\omega$-Hydroxyarginine has the formula (I) where $R^1$, $R^2$ and $R^3$ are hydrogen, and $R^4$ is $(CH_2)_3CH(NH_2)COOH$.

Hydroxyguanidine has the formula (I) where $R^1$, $R^2$, $R^3$ and $R^4$ are all hydrogen.

$N^\omega$-Hydroxyarginine and hydroxyguanidine are available commercially.

Still other hydroxyguanidine treating agents include, for example, compounds of formula (I) where $R^1$, $R^2$ and $R^3$ are H, and $R^4$ is $(CH_2)_3C(CH_3)(NH_2)COOH$, e.g., $N^\omega$-hydroxy-L-α-methylarginine; compounds of the formula (I) where $R^1$, $R^2$ and $R^3$ are H, and $R^4$ is $(CH_2)_4CH(NH_2)COOH$, e.g., $N^\omega$-hydroxy-L-homoarginine; compounds of the formula (I) where $R^1$, $R^2$ and $R^3$ are H, and $R^4$ is $(CH_2)_4NH_2$; and compounds of the formula (I) where $R^1$, $R^2$ and $R^3$ are H, and $R^4$ is $(CH_2)_4COOH$.

The other hydroxyguanidines are prepared by methods well known in the art from hydroxylamine or other simple precursors.

Still other hydroxyguanidines have the formula (I) where $R^1$, $R^2$, and $R^3$ are hydrogen and $R^4$ is n-propyl, isopropyl or n-butyl, and the syntheses of these are described in Xian, M., et al, Bioorganic and Medicinal Chemistry 16, 3049–3055 (2002).

As indicated above, the agents are administered in a therapeutically effective amount. This amount is a premature vascular senescence ameliorating amount, that is an amount reducing, reversing, or stopping the progression of premature vascular senescence. For treatment of end stage renal disease, the therapeutically effective amount is a premature vascular senescence ameliorating amount where premature vascular senescence amelioration is manifested by reduction in or stopping of the progression of symptoms of cardiovascular diseases, such as coronary artery disease, peripheral vascular disease, clotting and stenosis of arterio-venous fistula in patients with end stage renal disease on hemodialysis. For treatment of poorly controlled diabetes mellitus, chronic renal diseases, systemic lupus erythematosus and Alzheimer's disease and other neurodegenerative diseases, the therapeutically effective amount is a premature vascular senescence ameliorating amount where premature vascular senescence amelioration is manifested by reduction in or a stopping of the progression of symptoms of cardiovascular diseases, such as coronary artery disease or peripheral vascular disease. For peripheral vascular disease, the therapeutically effective amount is a premature vascular senescence ameliorating amount where premature vascular senescence amelioration is manifested by a reduction in or a stopping of the progression of symptoms of peripheral vascular disease. Therapeutic amounts depend on the agent administered and can range, for example, from 0.01 μmol/kg to 2 mmol/kg. For $N^\omega$-hydroxyarginine, administration can be, for example, of a loading dose, e.g., of 20 mg/kg, followed by 1 to 10 mg/kg/hr. Other suitable dosage information for $N^\omega$-hydroxyarginine is exemplified in the working examples hereinafter.

The hydroxyguanidines can be administered in admixture with antioxidant agents and vitamins (e.g., ascorbate, alpha-tocopherol, vitamin B6, vitamin B12, folate (folic acid), carotenoids, coenzyme Q10, phytoestrogens (including isoflavonoids), selenium, butylated hydroxytoluene (BHT), butylated hydroxyanisole (BHA) and n-3 polyunsaturated fatty acids (PUFA)) with or without L-arginine supplementation (20 mg/kg every 4 hours), as a nutriceutical.

The routes of administration include oral, transdermal, intravenous, and intramuscular.

We turn now to the second embodiment herein, that is the embodiment directed at a method of preventing the occurrence of premature senescence in vascular tissue or vascular cells ex vivo comprising incubating the tissue or cells with a premature vascular senescence preventing effective amount of agent selected from the group consisting of premature vascular senescence preventing hydroxyguanidines and pharmaceutically acceptable salts thereof.

The vascular tissue or vascular cells are preferably obtained from saphenous vein or mammary artery and, in the case of cells, are preferably endothelial cells.

The test for determining premature vascular senescence preventing hydroxyguanidine is carried out as follows: Vascular grafts are treated with the hydroxyguanidine agent being tested. Reduced SA-β-galactosidase staining of the graft, together with reduced stenotic and thrombotic complications as compared to untreated grafts indicates a premature vascular senescence preventing hydroxyguanidine.

The premature vascular senescence preventing agents are preferably the same as the premature vascular senescence ameliorating hydroxyguanidines of the first embodiment herein, i.e., have the formula (I) where $R^1$, $R^2$, $R^3$ and $R^4$ are as described above and the pharmaceutically acceptable salts are those described in conjunction with the first embodiment of the invention herein.

The incubation is preferably carried out in a medium comprising saline or phosphate buffered saline at a temperature ranging from 4° C. to 37.5° C., preferably at 35° C., for a time period which is appropriate for the use to which the treated vascular tissue or cells are to be put, and is generally in the range of ½ hour to 4 weeks.

The premature vascular senescence preventing amount of premature vascular senescence preventing hydroxyarginine, that is the concentration of the hydroxyarginine to be provided in the incubation medium, is determined by trying a plurality of increasing concentrations and will differ depending on what particular hydroxyguanidine is used and in general typically ranges from 0.1 $\mu$M to 10 mM. For $N^\omega$-hydroxy-L-arginine a preferred concentration in the incubation medium ranges from 10 $\mu$g/dl to 10 mg/dl.

A particular use for the second embodiment is to provide cells for plating on a cardiac stent to provide a nonthrombogenic surface. The cells may be attached to the stent by a biocompatible adhesive matrix or other linking technology.

Other uses for the second embodiment include providing cultured cells on an artificial heart valve or for seeding on artificial vascular grafts for femoral-to-poplital bypass surgery in a patient with peripheral vascular disease, so that the patient experiences less thrombotic and atheroembolic complications.

An alternative to the stent treatment described above is to covalently bond the hydroxyguanidine to a biodegradable polymer, e.g., polylactic acid, and to coat the product onto the stent.

The invention herein is supported by the following background example and is illustrated by the following working examples.

BACKGROUND EXAMPLE 1

Detection of SA-$\beta$-galactosidase was carried out utilizing the histochemical staining method of Dimitri et al, Proc. Natl. Acad. Sci. USA 92, 9363–9367 as modified by Van der Loo, B., et al, Exp. Cell Res. 241, 309–315 (1998). SA-$\beta$-galactosidase is a known senescence marker. En face SA $\beta$-galactosidase staining of aortas derived from age-matched Zucker diabetic and Zucker lean rats revealed that the former exhibited an uniform accumulation of senescent endothelial cells, especially at the branching points of daughter vessels—24 out of 24 branches studied showed SA $\beta$-galactosidase staining. This phenomenon occurred in 12 week and 21 week-old diabetic rats, but was undetectable in age-matched Zucker lean rats (0/24 branches examined).

BACKGROUND EXAMPLE 2

Human umbilical vein endothelial cells (HUVEC) after four passages were plated on glycated collagen with the addition of 0.1 mM hydroxy-L-arginine vis-a-vis the same concentration of L-arginine. Application was made on day 1, 2 hours after plating. The extent of SA $\beta$-galactosidase staining was evaluated on days 3 and 5 of culture on a glycated or native matrix. In addition, to study the reversibility process, HUVEC were plated on glycated collagen for three days (time sufficient to induce premature senescence), and hydroxy-L-arginine was added every 12 hours, starting on day 3, and the cells were examined on day 5. Glycated collagen resulted in concentration-dependent increase in the proportion of SA $\beta$-galactosidase-positive cells after three days in culture. Addition of hydroxy-L-arginine to the culture medium, but not L-arginine, completely abolished the development of premature senescence in HUVEC grown on glycated collagen. Hydroxyl-L-arginine was able to reduce premature senescence at all dilutions of glycated collagen in contrast to L-arginine alone which failed to reverse premature senescence at higher concentrations of glycated matrix.

EXAMPLE I

A forty-three year-old male with end stage renal disease due to glomerulonephritis (or systemic lupus erythematosus, or polycystic kidney disease, of focal segmental glomerulosclerosis, or amyloidosis, or rapidly progressive renal disease) and receiving chronic hemodialysis has serum creatinine concentration of 10 mg/dl, hematocrit of 33%, blood pressure 175/105 mmHg and shows one of the following levels of AGE: elevated level of pentosidine (2.5 pmol/mg) or elevated level of Amadori serum albumin (40 U/ml). (In some cases, renal biopsy will be performed, which will directly disclose the deposition of AGE in the renal parenchyma and increased proportion of SA-beta-galactosidase-stained endothelial cells). The patient has a history of coronary artery disease (CAD) with recent coronary artery bypass surgery; however, his graft shows signs of stenosis. In addition, the patient has his arterio-veinous fistula revised 3 times due to clotting and stenosis. The patient is also complaining of a non-healing foot ulcer and intermittent claudication, both signs of peripheral vascular disease. The patient starts receiving hydroxy-L-arginine 1–20 mg/kg thrice/day and 6 months later shows significant subjective improvement of coronary symptoms, healing of foot ulcer, normalization of blood pressure and a decrease in pentosidine (1.7 pmol/mg) and/or Amadori serum albumin (30 U/ml).

EXAMPLE II

A thirty year-old patient with type I (alternatively, a 60 year-old patient with type 2) diabetes mellitus, past medical history of myocardial infarction, peripheral vascular disease, hypertension, proteinuria and non-healing foot ulcer, is receiving insulin, but patient is poorly compliant. Patient's fasting blood glucose level is 200 mg/dl. Additional laboratory findings include elevated Hgb A1c level (8.5%) as well as one of the following levels of AGE: elevated level of pentosidine (2.3 pmol/mg) or elevated level of Amadori serum albumin (41 U/ml). (In some cases, renal biopsy will be performed, which will directly disclose the deposition of AGE in the renal parenchyma and increased proportion of SA-beta-galactosidase-stained endothelial cells). The patient is started on hydroxy-L-arginine 1–20 mg/kg thrice/day and 6 months later shows significant subjective improvement of coronary symptoms (coronary angiogram may show either no further worsening of stenotic lesions or some degree of improvement), healing of foot ulcer, normalization of blood pressure and, a decrease in pentosidine (1.7 pmol/mg) and/or Amadori serum albumin (30 U/ml).

EXAMPLE III

A sixty-eight year old man with no known medical conditions has been experiencing a sustained loss of short-term memory for the past three years. His CBC, electrolytes and other plasma parameters of metabolic profile are within normal range. There is no vitamin deficiency, no abnormalities in liver function tests, and no previous history of cerebro-vascular accidents. Head computerized tomographic study showed no brain atrophy. Based on these findings the patient is diagnosed with Alzheimer's disease. Therapy with hydroxy-L-arginine is initiated at doses 1–20 mg/kg thrice/day alone or in combination with antioxidant agents and vitamins (e.g., ascorbate, alpha-tocopherol, vitamin B6, vitamin B12, folate (folic acid), carotenoids, coenzyme Q10, phytoestrogens (including isoflavonoids), selenium, butylated hydroxytoluene (BHT), butylated hydroxyanisole (BHA) and n-3 polyunsaturated fatty acids (PUFA)). Two years later the patient shows no deterioration and a partial improvement of symptoms related to the memory loss.

EXAMPLE IV

Positive results similar to those obtained in Examples I, II and III are obtained when the same dosage of hydroxyguanidine or of the n-propyl, isopropyl or n-butyl substituted hydroxyguanidines described above is substituted for the hydroxy-L-arginine.

EXAMPLE V

A sixty-five year-old woman with a defective heart valve is being prepared for a surgical replacement of the valve with a prosthetic device. A saphenous vein is obtained to harvest endothelial cells for expansion and seeding on the surface of a artificial valve. Expanded endothelial cells are cultured in the medium containing hydroxy-L-arginine, 10–100 $\mu$g/ml at 35° C. for 2–3 weeks and cells are seeded on the valve in the continuous presence of the same concentration of hydroxy-L-arginine. Thus prepared, the artificial valve is implanted. The patient experiences less thrombotic and atheroembolic complications and may require lower doses of anticoagulants.

EXAMPLE VI

A seventy-two year old man with peripheral vascular disease is undergoing an elective femoral-to-popliteal bypass surgery utilizing an artificial vascular graft. A saphenous vein is obtained to harvest endothelial cells for expansion and seed on the surface of a graft. Expanded endothelial cells are cultured in the medium containing hydroxy-L-arginine, 10–100 $\mu$g/ml at 35° C. for 2–3 weeks, and cells are seeded on the graft in the continuous presence of the same concentration of hydroxy-L-arginine. Thus prepared, the vascular graft is implanted. The patient experiences less thrombotic and atheroembolic complications and may require lower doses of anticoagulants.

VARIATIONS

Variations on the above will be obvious to those skilled in the art. Thus, the scope of the invention is defined by the claims.

What is claimed is:

1. A method of treating an animal with elevated levels of advanced glycation end products in blood or tissue comprising administering to the animal a therapeutically effective amount of agent which is selected from the group consisting of premature vascular senescence ameliorating hydroxyguanidines selected from the group consisting of hydroxy-L-arginine and hydroxyguanidine and pharmaceutically acceptable salts thereof 2. The method of claim 1 where the animal is affected with end stage renal disease.

3. The method of claim 1 where the animal is affected with poorly controlled diabetes.

4. The method of claim 1 where the animal is affected with chronic renal disease.

5. The method of claim 1 where the animal is affected with peripheral vascular disease.

6. The method of claim 1 where the animal is affected with systemic lupus erythematosis.

7. The method of claim 1 where the animal is affected with Alzheimer's disease.

8. The method of claim 1 where the animal is affected with a disorder selected from the group consisting of end stage renal disease, chronic renal disease, poorly controlled diabetes, peripheral vascular disease, systemic lupus erythematosis and Alzheimer's disease.

9. The method of claim 8 wherein the agent comprises hydroxy-L-arginine.

10. The method of claim 8 wherein the disorder is selected from the group consisting of end stage renal disease, chronic renal disease, perpheral vascular disease and systemic lupus erythematosis.

11. The method of claim 10 where the agent comprises hydroxy-L-arginine.

* * * * *